United States Patent [19]
Fayerman et al.

[11] Patent Number: 4,880,735
[45] Date of Patent: Nov. 14, 1989

[54] PROCESS FOR PRODUCING ANTIBIOTIC A47934

[75] Inventors: Jeffrey T. Fayerman; Michael D. Jones; Karl H. Michel, all of Indianapolis; Raymond C. Yao; Milton J. Zmijewski, both of Carmel, all of Ind.

[73] Assignee: Eli Lilly and Company, Indianapolis, Ind.

[21] Appl. No.: 911,180

[22] Filed: Sep. 24, 1986

[51] Int. Cl.[4] .................... C12P 21/04; C12P 17/18; C12R 1/465
[52] U.S. Cl. .................................. 435/71; 435/119; 435/253.5; 435/886
[58] Field of Search ............... 435/71, 886, 253, 119, 435/70, 253.5

[56] References Cited
U.S. PATENT DOCUMENTS

| 4,169,140 | 9/1979 | Ohba | 424/117 |
| 4,659,660 | 4/1987 | Hamill | 435/253 |

OTHER PUBLICATIONS

J. T. Fayerman et al., "Development of Systems for Heterlogous Gene Expression in Streptomyces spp.," *Microbiology*, 1985, 414–420.

Primary Examiner—Charles F. Warren
Assistant Examiner—Irene Marx
Attorney, Agent, or Firm—Nancy J. Harrison; Leroy Whitaker

[57] ABSTRACT

Improved fermentation process for producing the Gram-positive antibiotic A47934 which comprises cultivating a new strain of *Streptomyces toyocaensis*, NRRL 18112, and a biologically purified culture of this microorganism are provided.

3 Claims, No Drawings

PROCESS FOR PRODUCING ANTIBIOTIC A47934

SUMMARY OF THE INVENTION

This invention relates to a new microorganism, *Streptomyces toyocaensis* NRRL 18112, which is an improved producer of antibiotic A47934.

The new microorganism produces A47934 in substantially greater amounts than the prior art culture does. As a consequence, this invention also relates to an improved process for producing A47934 by culturing the new *Streptomyces toyocaensis* NRRL 18112 strain under submerged aerobic fermentation conditions until a substantial level of A47934 is produced. Antibiotic A47934 can be extracted from the fermentation broth, separated and purified by techniques in the art.

The new microorganism is also particularly receptive toward certain useful plasmids and is, therefore, valuable as a cloning host.

DETAILED DESCRIPTION OF THE INVENTION

Improved methods for producing antibiotics are of great importance. Commonly, the culture isolated from the natural state (the "wild type") produces the antibiotic in low yield. Often, antibiotic production is erratic. Strains with enhanced potency and strains which consistently produce the antibiotic are, therefore, of great value.

This invention provides an organism which is improved in the ability to produce antibiotic A47934. A47934 is an antibacterial agent which is especially active against Gram-positive bacteria. It also promotes growth in poultry and swine and enhances feed-utilization efficiency in ruminants. A47934 and a method for producing it using another *Streptomyces toyocaensis* strain (NRRL 15009, also called the A47934.strain) are described by Robert L. Hamill and Ralph E. Kastner in U.S. Pat. No. 4,462,942, issued July 31, 1984.

In another aspect, this invention provides an improved process for preparing the antibiotic A47934 by culturing a new A47934-producing strain of *Streptomyces toyocaensis*, NRRL 18112, under submerged aerobic conditions in a suitable culture medium until a substantial amount of antibiotic activity is produced.

The organism of this invention is especially valuable as a cloning host. It is more receptive toward useful plasmids than the A47934.1 strain. The A80934 culture can be protoplasted and transformed with great efficiency and exhibits reduced restriction activity.

THE MICROORGANISM

The microorganism of this invention has been designated the A80934 culture. This strain was isolated from a soil sample from a manchineel tree in the Virgin Islands. The A80934 strain was studied and characterized by Frederick P. Mertz of the Lilly Research Laboratories. The new microorganism was classified as a strain of *Streptomyces toyocaensis*, Nishimura, Katagiri, Sato, Mayama and Shimaoka 1954 (ATCC 19814) after direct-laboratory comparison with the A47934.1 strain and comparison with published descriptions [Nishimura, et al., Japanese Patent No. 236,280 (1954) and E. B. Shirling and D. Gottlieb, "Cooperative Description of Type Cultures of Streptomyces," *Int. J. Syst. Bacteriol.* 18(2):174 (1968).

Methods Used

The methods followed were those recommended by the International Streptomyces Project (ISP) for the characterization of Streptomyces species [E. B. Shirling and D. Gottlieb, "Methods of Characterization of Streptomyces Species," *Int. J. Syst. Bacteriol.* 16(3):313–30 (1966)].

Morphology was studied using an optical light microscope. A scanning electron microscope (SEM) was used to study the spore surface ornamentation.

ISCC-NBS Centroid Color Charts, standard sample No. 2106 (National Bureau of Standards, 1958, U.S. Department of Commerce, Washington, D.C.) and the *Color Harmony Manual* (4th ed., Container Corporation of America, Color Standards Department, Chicago, Ill., 1958) were used to assign color names.

Melanoid pigment production (chromogenicity) was determined with ISP No. 1 (tryptone-yeast extract broth), ISP No. 6 (peptone-yeast extract iron agar) and ISP No. 7 (tyrosine agar) media.

The isomers of diaminopimelic acid (DAP) and the carbohydrates in hydrolysates of whole cells were established by the chromatographic methods of Becker et al. [B. Becker, M. P. Lechevalier, R. E. Gordon and H. A. Lechevalier, "Rapid Differentiation between Nocardia and Streptomyces by Paper Chromatography of Whole-cell Hydrolysates," *Appl. Microbiol.* 12(5), 214–423 (1964)] and of Lechevalier and Lechevalier [M. P. Lechevalier and H. Lechevalier, "Chemical Composition as a Criterion in the Classification of Aerobic Actinomycetes," *Int. J. Syst. Bacteriol.* 20 (4):435–443 (1970)].

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch) agar plates (See D. J. Blazevic and G. M. Ederer, *Principles of Biochemical Tests in Diagnostic Microbiology*, John Wiley and Sons, Inc., New York, 1975, p. 136).

Carbon utilization was determined on ISP No. 9 basal medium to which filter-sterilized carbon sources were added to equal a final concentration of 1.0 percent. Plates incubated at 30° C. and read after 14 days.

NaCl tolerance was measured by adding NaCl to ISP No. 2 agar to equal the concentration desired.

Cultural Characteristics

A80934 produces excellent vegetative and aerial growth on the media used in this study. The aerial hyphae have a spore-mass color in the gray (GY) color series. The nearest matching color tab in the Tresner and Backus system [H. D. Tresner and E. J. Backus, "System of Color Wheels for Streptomycete Taxonomy," *Appl. Microbiol.* 11:355–338 (1956)] is 2ih light olive gray. This is seen on all the media, but is best demonstrated on inorganic salts starch agar (ISP No. 4).

A80934 does not produce distinctive pigments on the reverse side of the colony, nor does it produce any soluble pigments. The color of the reverse side is dark grayish yellow on ISP No 4, and ranges from orangey-ellow on yeast malt extract agar (ISP No. 2) to moderate yellow brown on tomato paste oatmeal agar (TPO). The cultural characteristics observed in this study are summarized in Table No. I.

TABLE I

Cultural Characteristics of A80934 and A47934.1 on Various Agar Media[a]

| Agar Media | | A80934 | A47934.1 |
|---|---|---|---|
| ISP No. 2 | G: | Good | Abundant |
| | R: | 72.d.OY | 68.s.OY |
| | Am: | Good: (2ih) 1.01 Gray | Good: (2ih) 1.01 Gray |
| | Sp: | None | None |
| ISP No. 3 | G: | Fair | Good |
| | R: | 112. 1.01 Gy | 91.d.gy.Y |
| | Am: | Fair: (2ih) 1.01 Gray | Good: (2ih) 1.01 Gray |
| | Sp: | None | None |
| ISP No. 4 | G: | Abundant | Abundant |
| | R: | 91.d.gy.Y | 94.1.01 Br |
| | Am: | Abundant: (2ih) 1.01 Gray | Abundant: (2ih) 1.01 Gray |
| | Sp: | None | None |
| ISP No. 5 | G: | Abundant | Abundant |
| | R: | 90.gy.Y | 67.brill.OY |
| | Am: | Abundant: (2ih) 1.01 Gray | Good: (2ih) 1.01 Gray |
| | Sp: | None | None |
| Czapek's Agar | G: | Good | Good |
| | R: | 91.d.gy.Y | 91.d.gy.Y |
| | Am: | Good: (2ih) 1.01 Gray | Good: (2ih) 1.01 Gray |
| | Sp: | None | None |
| Tomato paste oatmeal agar | G: | Abundant | Abundant |
| | R: | 77.m.yBr | 94.1.01Br |
| | Am: | Abundant: (2ih) 1.01 Gray | Abundant: (2ih) 1.01 Gray |
| | Sp: | None | None |

[a]G = growth;
R = reverse;
Am = aerial mycelium;
Sp = soluble pigment

Morphological Characteristics

Strain A80934 produces well developed non-fragmenting aerial mycelia which are monopodially branched. Sporophores are arranged in open, short, loose spirals of 2 to 3 coils. It is therefore placed in the Spirales (S) section of Pridham [T. G. Pridham, C. W. Hesseltine, and R. G. Benedict, "A Guide for the Classification of Streptomycetes According to Selected Groups," *Appl. Microbiol.* 6:52–79 (1957)].

This spiral morphology is seen on all the media tested. Glycerol asparagine agar (ISP No. 5) exhibits this especially well.

Mature spore chains generally contain from 10 to 50 spores per chain. The spore shape is oblong to oval and has an average size of 12.0×9.8 μM. The spore surface ornamentation is spiny (Spy).

Physiological Characteristics

Analysis of hydrolyzed whole cells indicated the presence of L-diaminopimelic acid (LL-DAP) with no meso isomer present. Sugar analysis of hydrolyzed whole cells indicated the presence of glucose and ribose. This represents a type I cell wall and a type C sugar pattern, which is indicative of the genus Streptomyces (Lechevalier and Lechevalier, supra).

The carbon-utilization pattern is summarized in Table II.

TABLE II

Utilization of Carbon Sources by Strains A80934 and A47934.1[a]

| Carbon Source | A80934 | A47934.1 |
|---|---|---|
| None | − | − |
| D-Glucose | + | + |
| L-Arabinose | + | + |
| Cellobiose | + | + |
| D-Fructose | + | + |
| D-Galactose | + | + |
| i-Inositol | + | + |
| D-Mannitol | − | − |
| Melibiose | − | − |
| Raffinose | − | − |
| L-Rhamnose | − | − |
| Ribose | + | + |
| Salicin | + | − |
| Sucrose | − | − |
| D-Xylose | + | + |

[a]+ = uses source
− = doesn't use source

Culture A80934 is resistant to cephalothin (30 μg), lincomycin (2 μg), penicillin G (10 units), rifampin (5 μg) and streptomycin (10 μg). It is sensitive to bacitracin (10 units), gentamicin (10 μg), neomycin (30 μg), oleandomycin (15 μg), tetracycline (30 μg), tobramycin (10 μg) and vancomycin (30 μg).

Strain A80934 will reduce nitrate to nitrite, hydrolyze starch, and produces catalase. It will tolerate up to 8% NaCl and will grown at temperatures between 15°–45° C. It does not produce melanoid pigments when grown in tryptone yeast extract broth (ISP No. 1), or on slants of peptone yeast extract iron agar (ISP No. 6) and tyrosine agar (ISP No. 7).

Species Determination

The cultural, morphological and physiological characteristics of A80934 were compared with those of strain A47934.1. Slight differences exist in carbon utilization (salicin), and NaCl toleration (8 versus 9%). Table III compares the two strains.

TABLE 3

Comparison of Characteristics of Strains A80934 and A47934.1

| Characteristic | A80934 | A47934.1 |
|---|---|---|
| Melanoid pigment | − | − |
| Temperature range - °C. | 15–45 | 15–40 |

TABLE 3-continued

| Comparison of Characteristics of Strains A80934 and A47934.1 | | |
|---|---|---|
| Characteristic | A80934 | A47934.1 |
| NaCl tolerance - % | 0–8 | 0–9 |
| Nitrate reduction | + | + |
| Starch hydrolysis | + | + |
| Aerial spore mass color | Gy | Gy |
| Morphology | S | S |
| Spore surface ornamentation | Spiny | Spiny |
| Spore shape | Oval | Oval |
| Spore size (average) μM | 12 × 9.8 | 0.8 × 0.6 |
| Catalase production | + | + |
| Cell-wall type | I | I |
| Cell-wall sugars: | glucose ribose | glucose ribose |
| Glycopeptide synthesis | + | + |

These comparisons indicate that A80934 is very similar to A47934.1, which has been classified as a strain of *Streptomyces toyocaensis*. Culture A80934 is, therefore, also classified as a strain of *S. toyocaensis* Nishimura, Katagiri, Sato, Mayama and Shimaoka 1954, type strain ATCC 19814.

*S. toyocaensis* was first described by Nishimura et al., supra, but no subsequent description followed. It is not listed in the Approved Lists of Bacterial Names [V. B. D. Skerman, et al., "Approved Lists of Bacterial Names," *Int. J. Syst. Bacteriol.* 30(1):225–420 (1980)] but it is fully described in the ISP study (Shirling and Gottlieb, 1968, supra) and elsewhere and is, therefore, a recognized taxon.

The A80934 strain of this invention has the identifying characteristics of the A47934.1 strain, but differs from it in the temperature range at which it grows, the utilization of salicin, the level of NaCl toleration, its receptivity towards plasmids and the amount of antibiotic A47934 produced. In shake-flask fermentation the improved A80934 strain of this invention produced at least 2 times the amount of antibiotic A47934 produced by the A47934.1 strain. With this enhanced A47934-producing characteristic, the new strain offers a greatly improved method for obtaining the antibiotic.

The new A80934 *Streptomyces toyocaensis* strain of this invention has been deposited and made a part of the stock culture collection of the Midwest Area Northern Regional Research Center, U.S. Department of Agriculture, Agricultural Research Service, Peoria, Ill., 61604, from which it is available to the public under the accession number NRRL 18112. The preceding *S. toyocaensis* strain A47934.1 is also available from this culture collection under the accession number NRRL 15009.

As is the case with other organisms, the characteristics of the new A47934-producing culture of this invention, *Streptomyces toyocaensis* NRRL 18112, are subject to variation. Recombinants, variants and mutants of the NRRL 18112 strain may be obtained by methods known in the art. For example, mutants may be obtained by treatment with various known mutagens such as ultraviolet rays, X rays, high-frequency waves, radioactive rays and chemicals. Recombinant strains can be obtained by transforming the *S. toyocaensis* strains using transformation techniques and recombinant vectors in the art. For example, the strains may be transformed with a recombinant vector that confers resistance to an antibiotic to which the strains are normally sensitive. Transformants thus obtained will produce not only antibiotic A47934 but also the resistance-conferring protein that allows selection of the transformants from wild-type cells. Using similar techniques, the strains can be modified to introduce multiple copies of the endogenous antibiotic-biosynthesis genes to achieve greater antibiotic yield. Natural and induced variants, mutants and recombinants of *Streptomyces toyocaensis* NRRL 18112 which retain either the characteristic of enhanced A47934 antibiotic production or the characteristic of increased receptivity toward plasmids are a part of this invention.

This invention also relates to an improved process for producing antibiotic A47934 which comprises culturing *Streptomyces toyocaensis* NRRL 18112, or an A47934-producing mutant, variant or recombinant thereof, in a culture medium containing assimilable sources of carbon and nitrogen under submerged aerobic fermentation conditions until a substantial amount of A47934 is produced.

The culture medium used to grow the *Streptomyces toyocaensis* NRRL 18112 culture can be any one of a number of media. For economy in production, optimal yield and ease of product isolation, however, certain culture media are preferred. Thus, for example, suitable carbon sources include potato dextrin, tapioca dextrin, glucose, corn starch, molasses and the like. Suitable nitrogen sources include enzyme-hydrolyzed casein, beef extract, soybean meal, soybean grits and the like. Nutrient inorganic salts which can be incorporated in the culture media are the soluble salts capable of yielding potassium, ammonium, chloride, sulfate, nitrate and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (e.g., 0.2 ml/L) of an antifoam agent such as polypropylene glycol to large-scale fermentation media if foaming becomes a problem.

For production of substantial quantities of antibiotic A47934, submerged aerobic fermentation in tanks is preferred. Small quantities of A47934 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank.

The new A47934-producing organism can be grown at temperatures between about 15° and about 45° C. Optimum A47934 production appears to occur at a temperature of about 30° C.

As is customary in aerobic submerged culture processes, sterile air is dispersed through the culture medium. For efficient production of A47934, the percent of air saturation for tank production should be above 20%, preferably above 30% (at 30° C. and one atmosphere of pressure).

Production of A47934 can be followed during the fermentation by testing samples of the broth for antibiotic activity against organisms known to be sensitive to A47934. One useful assay organism is *Bacillus subtilis*.

The A47934 produced by this method can be recovered by methods known in the art (see U.S. Pat. No. 4,537,879).

Alternatively, the culture solids, including medium constituents and mycelium can be used without extraction or separation, but preferably after removal of water, as a source of antibiotic A47934. For example, after production of A47934, the culture medium can be dried by lyophilization and mixed directly into feed premix.

In order to illustrate the operation of this invention more fully, the following example is provided.

EXAMPLE 1

Shake Flask Fermentation of A80934

A lyophilized pellet of *Streptomyces toyocaensis* NRRL 18112 was dissolved in 1–2 mL of sterilized water. This solution was used to inoculate a vegetative medium having the following composition:

| Vegetative Medium | |
|---|---|
| Ingredient | Amount (g/L) |
| Glucose | 15.0 |
| Potato dextrin | 20.0 |
| Soybean grits | 15.0 |
| Yeast extract | 1.0 |
| Corn steep liquor | 10.0 |
| $CaCO_3$ | 2.0 |
| Cold tap water, q.s. to 1 L | |
| Adjust pH to 6.5 with 5N NaOH | |

The inoculated vegetative medium (50 mL) was incubated in a 250-mL Erlenmeyer flask at 30° C. for 48 hours on a shaker rotating through an arc 2 inches in diameter at 250 rpm.

This incubated vegetative medium (0.5 mL) was used to inoculate 50 mL of a production medium having the following composition:

| Fermentation Medium | |
|---|---|
| Ingredient | Amount (g/L) |
| Glucose | 25.0 |
| Potato dextrin | 30.0 |
| Molasses | 3.0 |
| Soybean grits | 15.0 |
| Acid-hydrolyzed casein (casamino acid) | 1.0 |
| $CaCO_3$ | 2.5 |
| Cold tap water, q.s. to 1 L | |
| Adjust pH to 7.5 with 5N NaOH | |

The inoculated production medium was incubated in a 250-mL Erlenmeyer flask at 30° C. for 48 hours on a shaker rotating through an arc 2 inches in diameter at 250 rpm.

EXAMPLE 2

Isolation of A47934 Produced by Culture A80934

Fermentation broth (9 L), obtained as described in Example 1, was filtered. The filtrate was applied to a 5.5-30-cm column packed with HP-20 resin. The resin was washed with water (5 L) and $CH_3OH:H_2O$ (1:3, 2 L). The active material was eluted stepwise using $CH_3OH:H_2O$ (1:1). The two most active eluates were concentrated and freeze-dried to give crude A47934 (4.3 g and 1.5 g).

A portion of the 1.5-g preparation (150 mg) was dissolved in water (5 mL) and applied to a 22×300-mm glass column packed with LP-1/$C_{18}$ reversed-phase silica gel (10–20μ, see U.S. Pat. No. 4,299,763). The column was developed using a 0.5M aqueous $NH_4H_2PO_4:CH_3CN$ solvent system in a gradient of 9:1 (500 mL) to 7:3 (500 mL) and collecting 7-mL fractions. Fractions were analyzed for the presence of A47934 using HPLC. A47934containing fractions were combined and desalted, using HP-20 resin. A47934-containing fractions were collected, concentrated and freeze-dried to give 22 mg of purified A47934 (identified by FAB/MS using glycerol and 2 mmol KCl and by HPLC).

EXAMPLE 3

Comparison of A47934 Production Using the A80934 and A47934.1 Strains

Antibiotic A47934 was produced and isolated via the procedure of Example 1 using both the A47934.1 and A80934 cultures (10 10-mL flasks of each culture). To each flask was added 1.0M Caps buffer pH 11 (2 mL). The solution was shaken and centrifuged at approximately 3500 rpm. Supernatant (4 mL) was removed and 1.0M phosphate pH 6 buffer (0.8 mL) was added. The amount of A47934 produced was determined by comparative HPLC assay, using the following HPLC system:

A47934 HPLC Assay

Column Support: Waters Nova C18 Radial-PAK with a C-18 guard pack insert

Injection: 10 μL of sample

Solvent: $CH_3CN:0.2\%$ triethylamine in distilled water adjusted to pH 3 with $H_3PO_4$

A=5:95

B=1:3

System: Gradient elution: 100% A to 45:55 (A:B) in 20 minutes; hold for 5 minutes; to 100% A in 3 minutes; hold for 7 minutes.

Flow rate: 1.0 mL/min

Detection: UV at 225 nm (LDC/Milton Roy Spectro-Monitor III)

Based on these assays, the following amounts of antibiotic A47934 were produced by cultures A47934.1 and A80934:

TABLE IV

Comparison of A47934 Production by Cultures A47934.1 and A80934

| Culture | Standard | Retention Time (min) | Amount of A47934 Produced (mg/mL)[a] |
|---|---|---|---|
| — | A47934 | 17.98 | — |
| A47934.1 | | 17.98 | 0.33 |
| " | | 18.00 | 0.38 |
| " | | 18.01 | 0.35 |
| " | | 18.01 | 0.28 |
| " | | 18.01 | 0.29 |
| " | | 18.00 | 0.26 |
| " | | 17.97 | 0.28 |
| " | | 17.92 | 0.31 |
| " | | 17.93 | 0.25 |
| " | | 17.94 | 0.36 |
| — | A47934 | 17.91 | — |
| A80934 | | 17.91 | 0.78 |
| " | | 17.92 | 0.78 |
| " | | 17.92 | 0.78 |
| " | | 17.91 | 0.77 |
| " | | 17.91 | 0.75 |
| " | | 17.92 | 0.75 |
| " | | 17.93 | 0.75 |
| " | | 17.91 | 0.70 |
| " | | 17.91 | 0.77 |
| " | | 17.90 | 0.73 |

TABLE IV-continued

Comparison of A47934 Production by Cultures A47934.1 and A80934

| Culture | Standard | Retention Time (min) | Amount of A47934 Produced (mg/mL)[a] |
|---|---|---|---|
| — | A47934 | 17.94 | — |

[a]Amount calculated by measuring area under HPLC peak and comparing with standard sample As Table IV shows, the amount of antibiotic A47934 produced by the A80934 culture is substantially greater than that produced by the prior at A47934.1 culture.

We claim:

1. A biologically purified culture of the microorganism *Streptomyces toyocaensis* NRRL 18112.

2. In the process for producing antibiotic A47934, the improvement which comprises cultivating a microorganism recited in claim 1 in the culture medium containing assimilable sources of carbon and nitrogen under submerged aerobic fermentation conditions until antibiotic A47934 is produced.

3. The process of claim 2 which includes the additional step of separating antibiotic A47934 as a complex from the culture medium.

* * * * *